(12) United States Patent
Sinha

(10) Patent No.: US 7,499,808 B2
(45) Date of Patent: Mar. 3, 2009

(54) METHOD AND SYSTEM FOR CHARACTERIZING NANOPARTICLES IN A GUN-SHOT RESIDUE

(76) Inventor: Saion K. Sinha, 95 Nichols Ave., Fairfield, CT (US) 06825

( * ) Notice: Subject to any disclaimer, the term of this patent is extended or adjusted under 35 U.S.C. 154(b) by 199 days.

(21) Appl. No.: 11/414,997

(22) Filed: May 1, 2006

(65) Prior Publication Data

US 2007/0045243 A1 Mar. 1, 2007

Related U.S. Application Data

(60) Provisional application No. 60/676,801, filed on May 2, 2005.

(51) Int. Cl.
*G01N 33/00* (2006.01)
*G06F 17/00* (2006.01)

(52) U.S. Cl. .............. 702/27; 702/22; 702/29; 702/30; 702/32

(58) Field of Classification Search ............ 702/27, 702/22, 23, 29, 30, 32; 977/840, 849, 880, 977/881, 895
See application file for complete search history.

(56) References Cited

U.S. PATENT DOCUMENTS 6,613,576 B1 *  9/2003  Rodacy et al. ............ 436/164
6,640,132 B1 * 10/2003  Freeman et al. .......... 600/476
7,068,808 B1 *  6/2006  Prokoski ................... 382/100
2005/0057797 A1 * 3/2005  Treado et al. ............. 359/368

OTHER PUBLICATIONS

Hsien-Hui Meng et al., "The analysis of primer mixtures and gunshot residues using scanning electron microscopy/energy dispersive X-ray analysis", Oct. 14-16, 2003, IEEE 37th Annual 2003 International Carnahan Conference on Security Technology, 2003. Proceedings, pp. 358-363.*

Germani, "Evaluation of Instrumental Parameters for Automated Scanning Electron Microscopy/Gunshot Residue Particle Analysis", Mar. 1991, Journal of Forensic Sciences, vol. 36, No. 2, pp. 331-342.*

Peeters et al., "Automation of Gunshot-Residue Analysis by Functional Integration of a Scanning Electron Microscope and an Energy Dispersive Microanalysis System", 1990, Microbeam Analysis, pp. 369-371.*

Kosanke et al., "Characterization of Pyrotechnic Reaction Residue Particles by SEM/EDS", May 2003, Journal of Forensic Sciences, vol. 48, No. 3, pp. 531-537.*

* cited by examiner

*Primary Examiner*—Hal D Wachsman
(74) *Attorney, Agent, or Firm*—Sawyer Law Group LLP

(57) ABSTRACT

A method and system for characterizing gun-shot residue. More particularly, embodiments of the present invention provide a method that includes determining a size and an elemental composition of at least one nanoparticle from the gun shot residue and computing a temperature of formation of the at least one nanoparticle based on the size and the elemental composition of the at least one nanoparticle.

29 Claims, 6 Drawing Sheets

METHOD AND SYSTEM FOR CHARACTERIZING NANOPARTICLES IN A GUN-SHOT RESIDUE

CROSS-REFERENCE TO RELATED APPLICATIONS

This application claims benefit under 35 USC 119(e) of Provisional Application No. 60/676,801, filed on May 2, 2005.

FIELD OF THE INVENTION

The present invention relates to forensics, and more particularly to a method and system for characterizing gun-shot residue.

BACKGROUND OF THE INVENTION

Gun-shot residue plays an important role in forensic science in helping to determine certain factors of a shooting and/or related criminal cases. Gun-shot residue (GSR) is caused by the combustion involved in the firing of ammunition. When a gun is fired, the trigger of the gun is pulled causing a firing pin to strike the ammunition (i.e., bullet), crushing the primer. The energy transfer causes the explosion of the gun powder sending the bullet through the barrel. The velocity of the bullet is stabilized by a spiraling motion caused by lands and grooves in the barrel called riflings. In a crime laboratory, the riflings are used to match a bullet to a particular gun provided the bullet-shell is found at the crime scene. GSR is not only created as a cloud in the direct vicinity of the gun, but GSR is also propelled in the wake of the bullet in the direction of the target. GSR is obtained from every shooting incident and needs to be analyzed.

One conventional test for analyzing GSR is a chemical test, called the Modified Griess Test. The Modified Griess Test is a test to detect the presence of nitrite residues, and is the primary test used by firearms examiners to determine a muzzle-to-garment distance. The Modified Griess Test is performed first on the GSR since the test will not interfere with later tests for lead residues. Nitrite residues are a byproduct of the combustion of smokeless gunpowder. When a gun is discharged, nitrite particles are expelled from the muzzle of a gun and can be imbedded in, or deposited on, the surface of a target. Another conventional test conducted on GSR is called the Sodium Rhodizionate Test, which is a chemical test designed to determine if lead residues are present on the exhibit.

A problem with both the Modified Griess Test and the Sodium Rhodizionate Test is that most shooting cases involve firing at close range, and these tests are not applicable to shootings at close ranges (e.g., less than 5 feet). These techniques can only observe microscopic particles (particles whose diameter is a few microns or more) that are formed at distances of 5 feet or longer from the gun. Currently the GSR patterns are experimentally matched with the patterns at the crime scene on test firing. This is a time consuming and expensive process, and, again, does not work for short distances since it is difficult to observe a pattern in such a short distance. Moreover, these techniques require substantial amounts of GSR samples, which are difficult to obtain and are frequently contaminated. Accordingly, conventional techniques used for GSR analysis are limited, so prosecuting and defense attorneys typically rely on other evidence such as cartridge case volume and witness testimony to build a given case.

Accordingly, what is needed is an improved method and system for analyzing gun-shot residue. The present invention addresses such a need.

SUMMARY OF THE INVENTION

A method and system for characterizing gun shot residue is disclosed. The method includes determining a size and an elemental composition of at least one nanoparticle from the gun shot residue and computing a temperature of formation of the at least one nanoparticle based on the size and the elemental composition of the at least one nanoparticle. According to the method and system disclosed herein, the method and system provide valuable information for forensic studies.

DETAILED DESCRIPTION OF THE INVENTION

The present invention relates to forensics, and more particularly to a method and system for characterizing gun-shot residue. The following description is presented to enable one of ordinary skill in the art to make and use the invention, and is provided in the context of a patent application and its requirements. Various modifications to the preferred embodiment and the generic principles and features described herein will be readily apparent to those skilled in the art. Thus, the present invention is not intended to be limited to the embodiments shown, but is to be accorded the widest scope consistent with the principles and features described herein.

A method and system for characterizing gun shot-residue is disclosed. The method includes determining a size and an elemental composition of at least one nanoparticle from the gun shot residue and then computing the temperature of formation of the at least one nanoparticle based on the size and the elemental composition of the at least one nanoparticle. The method further includes utilizing the size, elemental composition, and temperature of formation of the nanoparticle to determine information such as gun information (e.g., gun make, model, and caliber); velocity and temperature of the bullet, distance traveled by the bullet; and the position and the time (e.g., where and when) the bullet was fired. As a result, the method and system provide valuable information for forensic studies. To more particularly describe the features of the present invention, refer now to the following description in conjunction with the accompanying figures.

Figure 1:
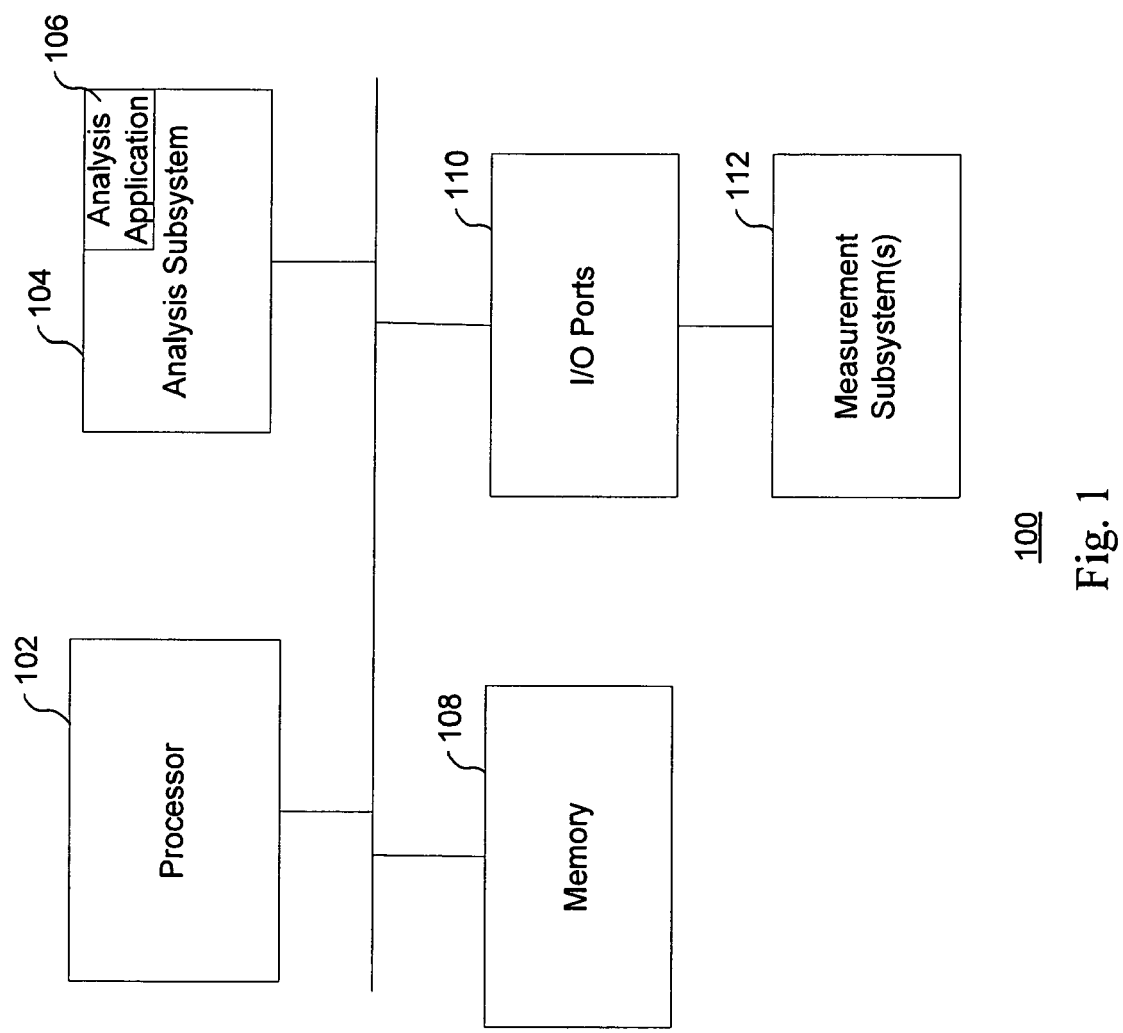
FIG. 1 is a block diagram of a system for analyzing gun-shot residue in accordance with the present invention.

FIG. 1 is a block diagram of a system 100 for analyzing gun-shot residue in accordance with the present invention. The system 100 includes a processor 102, an analysis subsystem 104, and an analysis application 106. In one embodiment, system 100 may also include a memory 108, input/ output ports 1010, and one or more measurement subsystems 112. While FIG. 1 shows the analysis application 106 being stored in the analysis subsystem 104, the analysis application 106 may be stored in the memory 108 or any suitable location. In operation, generally, in one embodiment, the analysis application 106 of the analysis subsystem 104 utilizes the processor 102 to analyze gun-shot residue. The operation of the system 100 is described in more detail below.

Figure 2:
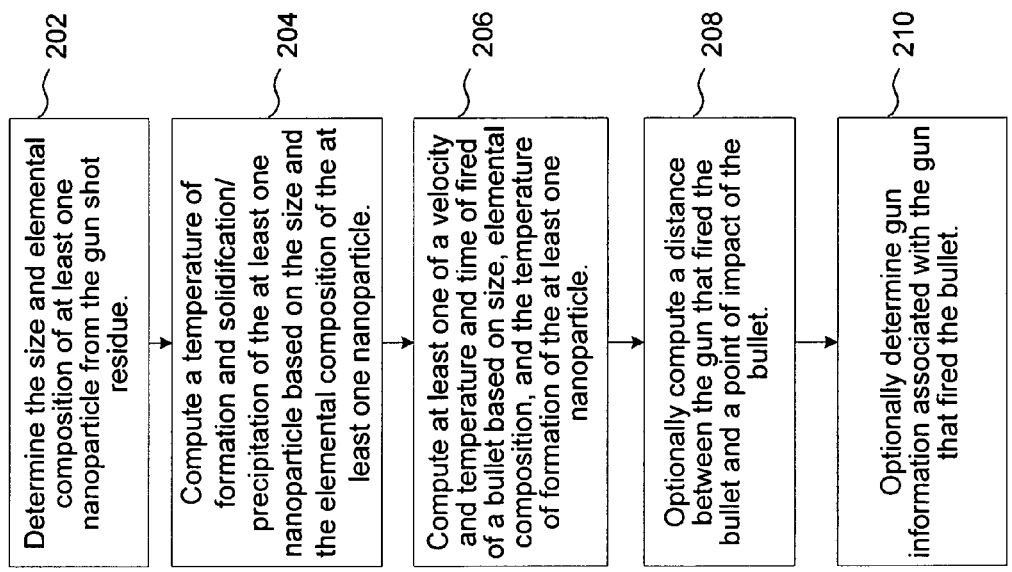
FIG. 2 is a flow chart showing a method for analyzing gun-shot residue in accordance with the present invention.

FIG. 2 is a flow chart showing a method for analyzing gun-shot residue in accordance with the present invention. Referring to both FIGS. 1 and 2, in a step 202, the analysis application 106 determines the size and elemental composition (e.g., percentage of lead (Pb) content) of at least one nanoparticle from the gun-shot residue. A nanoparticle is a particle having a diameter of approximately 100 nm. In one embodiment, one or more measurement subsystems 110 such as a scanning electron microscope (SEM) or an energy dispersive X-ray (EDX) may be utilized to characterize nanoparticles (i.e., facilitate in determining the size and elemental composition of the nanoparticle). Although the present invention disclosed herein is described in the context of a SEM or an EDX, the present invention may utilize other types of measurement devices, and still remain within the spirit and scope of the present invention.

In one embodiment, the characterization of the nanoparticle may be performed manually. In an alternative embodiment, the characterization of the nanoparticle may be automated. For example, in one implementation, the analysis application 106 may include modules for detecting brightness and contrast ratio (indicating nanoparticle boundaries) in a SEM image to automatically perform size measurements. Fast Fourier Transform (FFT) and other signal processing algorithms can be used to improve the signal to noise ratio of the observed SEM image. In one implementation, the analysis application 106 may also include modules for image processing algorithms for comparing, deconvulating, and mapping captured images to known images to automatically determine particle size and shape. In one implementation, the analysis application 106 may also include convulating the EDX-spectroscopy data for comparing and mapping captured peaks to standard database to automatically determine the elemental composition. In one implementation, such known images may be stored in the memory 108, a database (not shown), or other suitable location. Principles and related experiments regarding size and elemental composition are described in detail below in connection to FIGS. 3A-5.

Referring again to FIG. 2, in a step 204, the analysis application 106 then compute the temperature of formation and solidification/precipitation of the nanoparticle (when the gun was fired), based on the size and the elemental composition of the at least one nanoparticle. Next, in a step 206, the analysis application 106 computes at least one of a velocity, temperature and time of fire of the bullet based on one or more of the temperature of formation of the nanoparticle, the size of the nanoparticle, and the elemental composition of the nanoparticle.

In accordance with the present invention, the analysis application 106 utilizes an algorithm to compute the temperature of formation of the nanoparticle (based on the size and the elemental composition of the at least one nanoparticle) and to compute the velocity and temperature of the bullet when fired (based on the size, elemental composition, and temperature of formation of the nanoparticle). In one embodiment, the analysis application 106 performs an algorithm that computes one or more of a surface energy, the Gibbs free energy change, and a diffusion rate associated with the size, the elemental composition, and the temperature of formation. These aspects, which are governed by thermodynamic and mechano-chemical processes that are mathematically/computationally modeled, are described in more detail below in connection with FIGS. 3A-5.

In accordance with the present invention, the analysis application 106 may utilize the computed velocity and temperature of a bullet to determine various types of information associated with the gun used to fire the bullet and the firing of the bullet. For example, referring again to FIG. 2, in a step 208, the analysis application 106 may optionally compute a distance between a gun that fired the bullet and a point of impact of the bullet. In accordance with the present invention, the analysis application 106 may compute distances as short as 12 feet or less, or even 5 feet or less. Such information is useful in forensic studies (e.g., determining the distance may further determine whether a shooting was a suicide, a murder, an accident, or done in self defense). The distance is usually determined based on the distribution of GSR, and, as described in more detail below, the distribution of GSR may vary depending on the type of gun and ammunition being used. For instance, shorter and lower velocity guns and cartridges do not usually discharge residue at far distances compared to longer length and higher velocity guns and cartridges. On the other hand, shorter and lower velocity guns and cartridges will deposit larger concentrations of GSR at shorter distances. Also, depending on the type of gunpowder used, a particle can be more or less aerodynamic and can travel further. Therefore, it is equally important to consider both the gun and ammunition used in a shooting incident.

Furthermore, in a step 210, the analysis application 106 may optionally determine gun information associated with a gun that fired the bullet based on the velocity and temperature of the bullet. For example, the gun information may include the make, model, and caliber of the gun used to shoot the bullet, as well as the position and the time (e.g., where and when) the bullet was shot. Such determinations are possible, since thermodynamic and mechano-chemical processes (described in more detail below) are dependent on the gun energy, and the temperature of the GSR nanoparticle sizes depend on the type of the gun used. Principles and related experiments regarding these relationships are described in detail below in connection to FIGS. 3A-5.

Gun-Shot Residue Principles

Upon firing a gun, both burned and unburned powder and primer particles form a cloud that may cause a roughly circular pattern around the bullet hole upon contact. These particles, along with smoke, soot, and lead shavings are called gun shot residue, or GSR. While the vast majority of GSR is found in the six to eight inch muzzle-to-target range, GSR may also be found up to thirty six inches away. These ranges are considered a short range and a long range, respectively, with the medium range spanning eight to eighteen inches.

Firing a given gun (and ammunition) like those used in an actual incident sets the standard for characterizing the GSR of that gun at different distances. Firing the gun produces gunshot residue patterns that represent a minimum and a maximum firing distance. GRSs emitted from the muzzle will travel out to distances of approximately 3 to 5 feet in most guns, but in some cases can travel even greater distances. At the 3 to 5 foot range the gunshot residues may only consist of a few trace particles, and this makes determining the firing distance difficult if not impossible. As the gun gets closer to its target, the residue concentrations increase and the actual size (i.e., diameter of the pattern) of the nanoparticles increase. At distances of less than approximately 12 inches, a heavy concentration of visible gunshot residues will normally be deposited, which seems to be an advantage for short distance determinations. The reason short distance determinations may not be as common is possibly because when the muzzle of the gun gets next to or is in contact with the target, hot gases escaping from the muzzle at high velocity will typically rip, tear, shred, and/or melt the material of the target.

Electron microscopic experiments of the metallic nanoparticles 10 nm to 100 nm in diameter obtained from GSR at different target distances from a number of different types of hand guns have been analyzed and contrasted in detail. These experiments are described below. GSR generally contains lead, barium, antimony, arsenic, bismuth, cadmium, copper, silver, and/or tin. The detection of these elements in a sample would indicate the sampled item had been in the direct vicinity of a discharged weapon as they are present in measurable concentrations. Because the combination of these elements is rarely found in nature in the concentrations being tested, these elements provide GSR-specific source discrimination. The precise elemental composition may vary with each ammunition manufacturer, and the complete chemical elemental composition of both the gunpowder and primer is not generally disclosed by the ammunition manufacturer. However, it is known that approximately half of the compounds found in GSR contain lead. Published articles have found evidence of lead and antimony or lead and barium combinations in few occupational residues, rendering these combinations consistent with but not unique to GSR. Various articles have been published dealing with the elemental composition of the GSR and the National Academies Press recently compiled a number of papers further discussing the specific guidelines for bullet lead elemental composition comparison.

Experiments

One gun, a Winchester 9 mm Luger (X9MMST147) with Silvertip Hollow Point ammunition, was fired from distances of 2.54 cm, 10.16 cm, 33.02 cm, and 50.8 cm (or 1", 4", 13", and 20") from the muzzle to the target into cotton targets equipped with strips of double sided graphite tape for GSR collection. According to Winchester's 1999 Ballistics Guide, this ammunition has a weight of 147 grains and a muzzle velocity of 1010 ft/s (307.85 m/s), which reduces to a velocity of 962 ft/s (293.22 m/s) at a distance of fifty yards (45.72 m). The energy of the ammunition at the muzzle is 333 ft-lbs (46 J), which reduces to 302 ft-lbs (41 J) at fifty yards (45.72 m). A similar experiment was performed with a 0.45 Colt and the GSR was also collected at the same distances as the Winchester. Both of the weapons have the same size (i.e., length) muzzle, but the Colt has a larger caliber (i.e., diameter) than the Winchester. This means that the Colt bullet is 0.45" in diameter, which is almost a factor of 2 greater than the Winchester, whose bullet diameter is 9 mm. The muzzle velocity for the Colt is 253 m/s (slightly different from the Winchester), but its energy is 485 J, which is almost a factor of 10 greater than the Winchester.

After all shots were fired, each piece of graphite tape was labeled with the date, shot number, and distance. Both of these samples were then analyzed using a SEM as is common protocol for crime laboratories. The analysis revealed spherical nanoparticles ranging between approximately 60-200 nm in size for the Winchester and spherical nanoparticles ranging between 150-250 nm for the Colt. The Colt nanoparticles were all clustered together while the Winchester Nanoparticles were isolated.

Figure 3B:
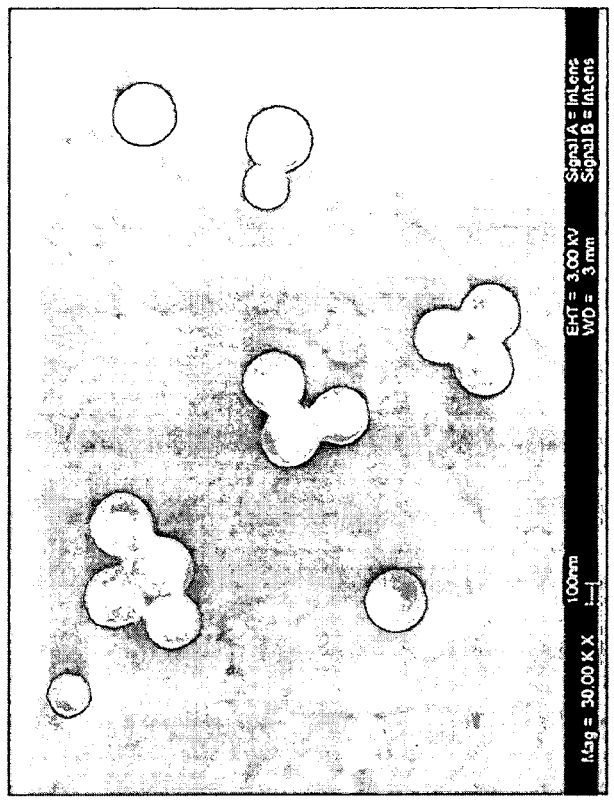
FIGS. 3A and 3B are scanning electron microscope (SEM) images showing the differences in nanoparticles of GSR formed at the same distance for two different types of guns, in accordance with the present invention.
Figure 3A:
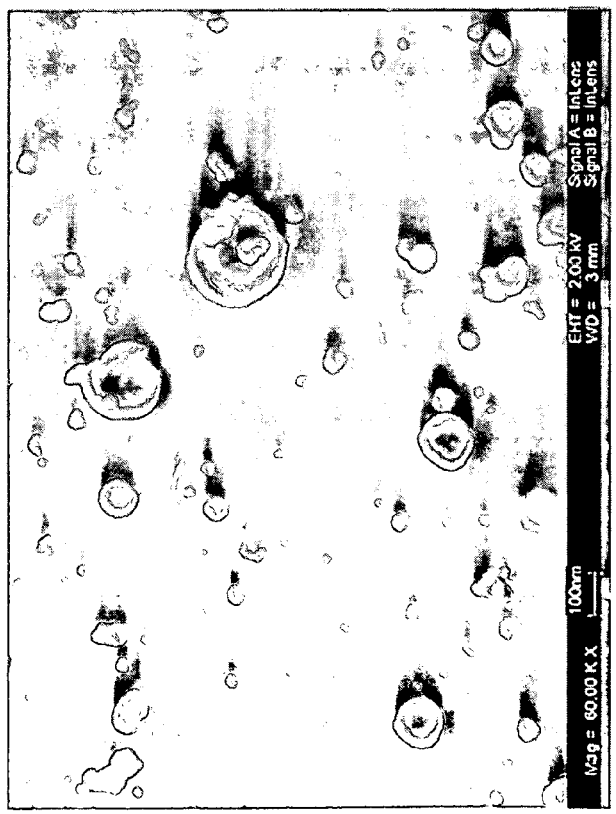

FIGS. 3A and 3B are SEM images showing the differences in nanoparticles of GSR formed at the same distance for two different types of guns—a 9 mm Winchester and a 0.45 Colt, respectively, in accordance with the present invention. The distance for both were collected at 2.54 cm (1") from the muzzle of the respective guns and the SEM images are the same magnification. Although some of the nanoparticles were damaged due to the force of impact, most were pure and spherical in form. In addition, the elemental analysis disclosed a correlation between the composition of lead and the distance from which the shots were fired. As the distance increased, the size of the nanoparticles increased proportionally, while the proportional amount of lead in the sample decreased. The following discussion describes these trends in more detail.

Figure 4A:
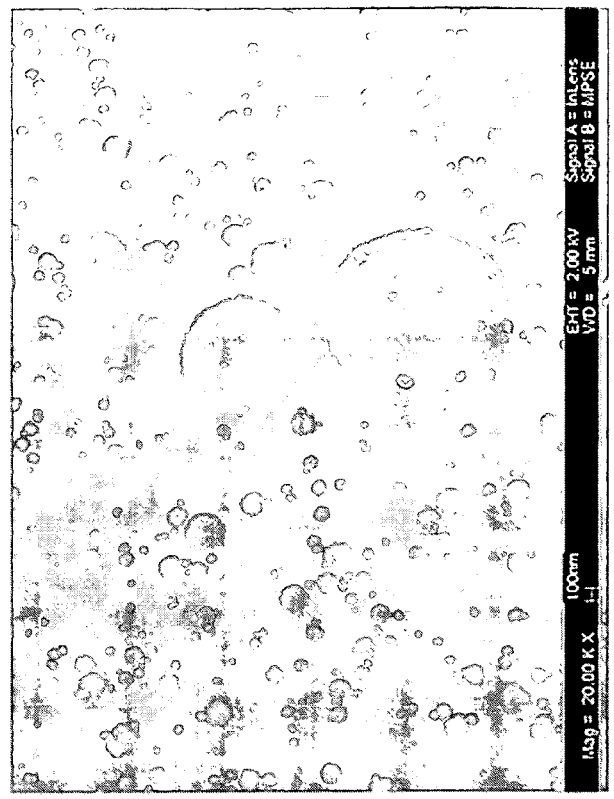
FIGS. 4A, 4B, 4C, and 4D are SEM images showing how nanoparticles grow in size as the muzzle-to-target distance increases for one type of gun, in accordance with the present invention.
Figure 4B:
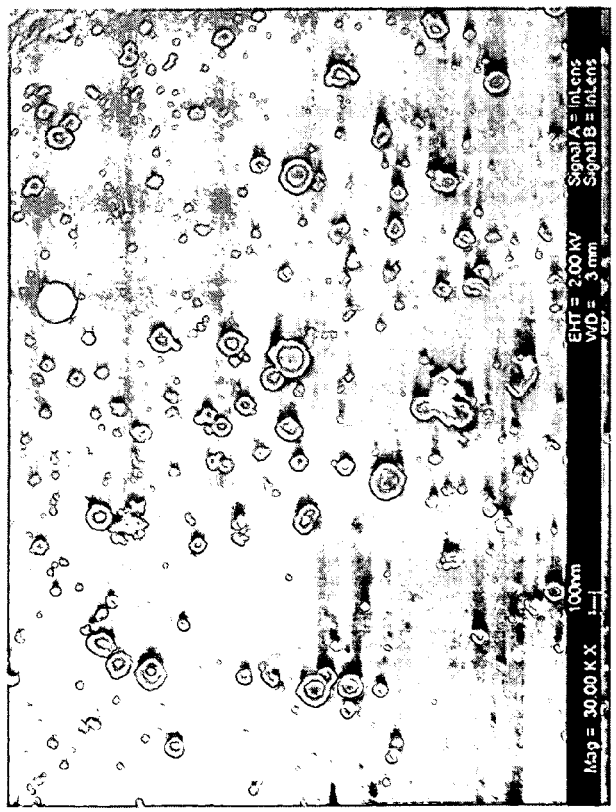
Figure 4D:
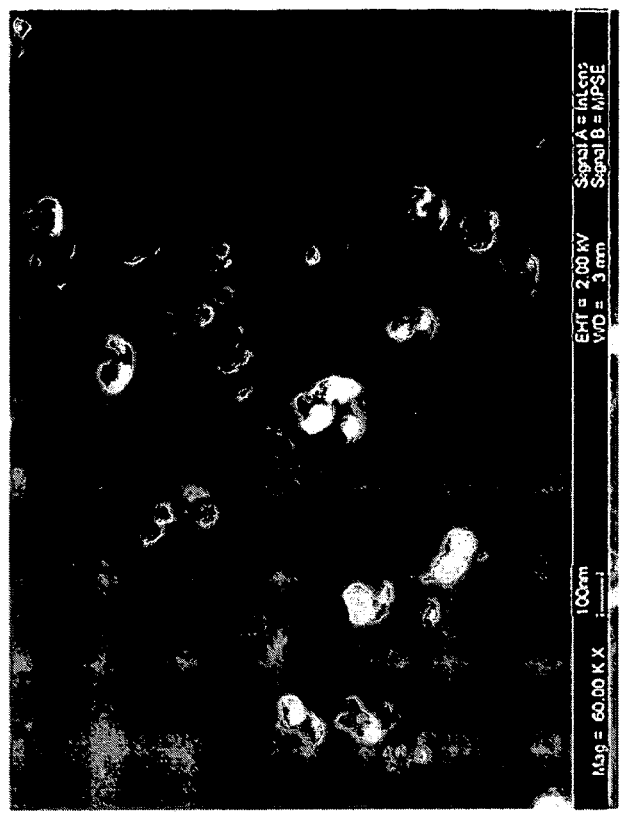
Figure 4C:
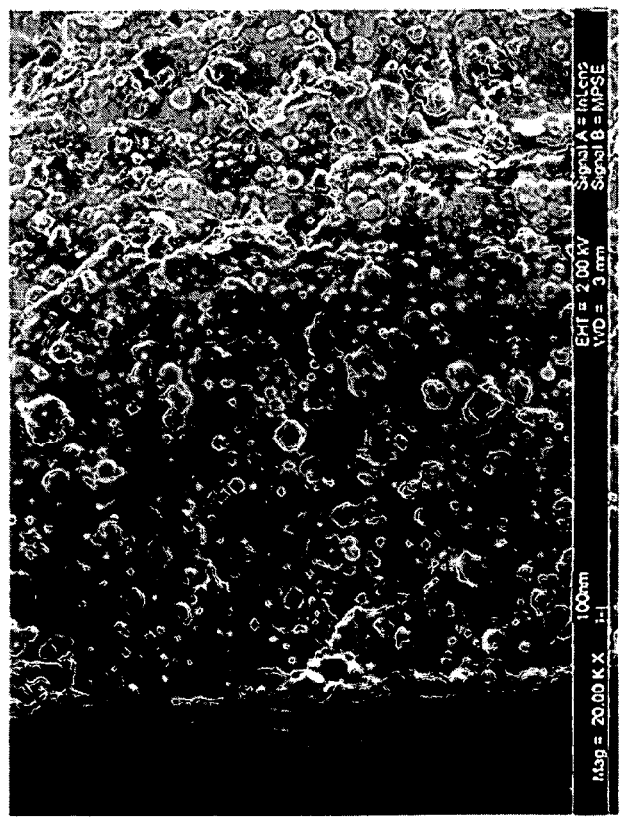

FIGS. 4A, 4B, 4C, and 4D are SEM images showing how nanoparticles grow in size as the muzzle-to-target distance increases for one type of gun—a Winchester, in accordance with the present invention. More specifically, FIG. 4A shows a SEM image of the lead nanoparticles where the muzzle-to-target distance is 2.54 cm (1"). The average diameter is 60 nm. FIG. 4B shows a SEM image where the muzzle-to-target distance is 10.16 cm (4"). The average diameter is 100 nm. FIG. 4C shows a SEM image where the muzzle-to-target distance is 33.02 cm (13"). The average diameter is 150 nm. FIG. 4D shows a SEM image where the muzzle-to-target distance is 50.8 cm (20"). The average diameter is 200 nm. Tests for the Colt produced similar trend where nanoparticles grow in size as the muzzle-to-target distance increases.

As FIGS. 4A-4D illustrate, nanoparticles are formed immediately after firing and these particles grow in size as they travel. For close distances (e.g., 5 feet for less), most of these particles are in the nanometer ranges. In addition to these findings, the elemental analysis of GSR has shown that the amount of lead decreases in proportion to the rest of the elements as the distance between muzzle and target increases. The spherical nanoparticles collected from a further distance were larger in diameter and fewer in quantity and are, therefore, consistent with a longer nucleation time.

These trends were first identified in a more casual overview of GSR, which was then refined into a precise and sterile protocol that was repeated for accuracy. As the analysis of GSR decreases in scale, the possible environmental contaminants become more relevant to the analysis. Since this correlation was seen in both the casual and formal experiment, it can be said that environmental addition of lead does not alter the general trend.

Figure 5:
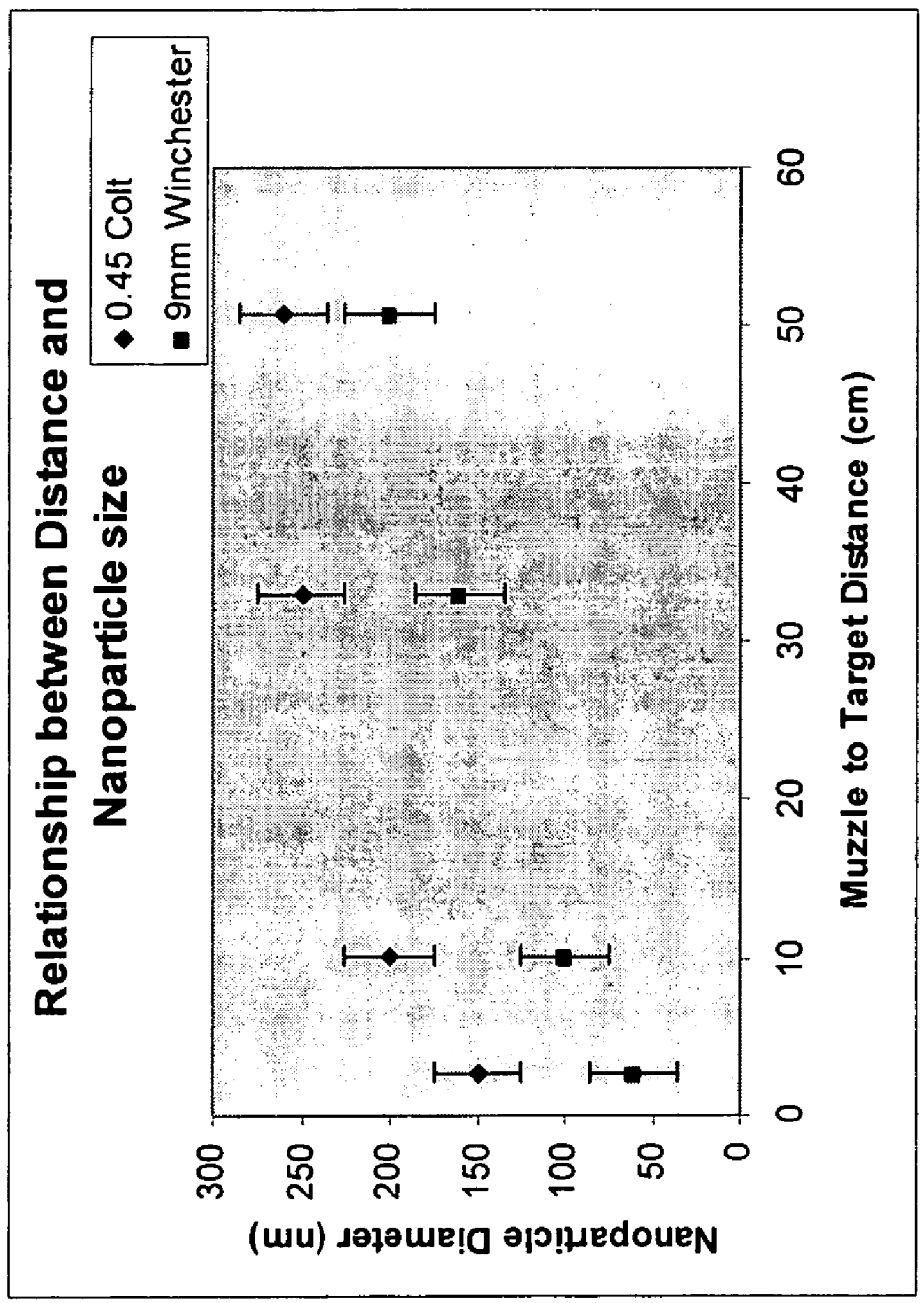
FIG. 5 is a graph illustrating a correlation between distance and nanoparticle size for two types of guns, in accordance with the present invention.

FIG. 5 is a graph illustrating a correlation between distance and nanoparticle size for two types of guns—a Winchester and a Colt, in accordance with the present invention. While the relationship between distance and size is linear for the Winchester, the relation between distance and the size for the Colt is not linear. The Colt nanoparticles are almost 30% larger than the Winchester nanoparticles for the shorter target-muzzle distance.

Principles as Applied to the Algorithm Performed by the Analysis Application

The theory behind the discussion above is that the exothermic chemical energy of combustion along with the mechanical energy caused by the impact of the firing pin on the bullet increases the temperature of the gun powder significantly above the melting points of the constituent metals. The lower melting point metals of the gun powder, like lead, are vaporized to a supersaturated vapor solution at this temperature. This plume of smoke cools very rapidly as it comes out of the barrel of the gun, thus generating VLS (Vapor-Liquid-Solid) type nanoparticle nucleation. As the nanoparticles move through this temperature gradient, the process of diffusion dominates the nucleation which results in the larger diameter of the nanoparticles.

A homogenous nucleation is assumed for lead nanoparticles by a VLS (Vapor-Liquid-Solid) mechanism as the nanoparticles exit a gun. The reduction of the Gibbs free energy is the driving force behind the nucleation and growth. The critical radius of a nanoparticle can be calculated from the following expression:

$$r = -2\frac{\gamma}{\Delta G_v} \quad (1)$$

The variable r is the critical radius, γ is the surface energy, and $\Delta G_v$ is the change in Gibbs free energy per unit volume of the Pb nanoparticle. The surface energy of the Pb nanoparticle can be assumed to be constant with reference to the size of the nanoparticles (50 nm-100 nm) in the experiment described above. Assuming the constant surface energy of the Pb nanoparticle to be 59 μJ/cm2, the Gibbs energy of formation is calculated to be 170 J/mol for the smallest (formed) nanoparticle. This is almost a factor of 1000 less than the Gibbs energy of formation of a bulk Pb crystal. In other words, the Gibbs free energy change is 1000 more times than elemental Pb crystal formation.

The lowering of the Gibbs energy is also related to the supersaturated solution by the following equation:

$$\Delta G_v = \frac{KT}{\Omega} \ln\left(\frac{C}{C_0}\right) \quad (2)$$

The variable C and $C_0$ are the concentration and the equilibrium concentration of the solute, respectively. The other variables in the equation are Boltzman Constant K, the temperature T, and the atomic volume Ω. Equation (2) may be used in the algorithm for calculating the temperature of formation. Using the Gibbs energy from equation (1) and assuming a temperature of 500K, it is observed that there is 50% more solute concentration in the nanoparticle formed at 20" (50.8 cm) than that formed at 2" (5.08 cm). Elemental analysis data on the GSR samples show a 48.5% increase in Pb concentration for the 50.8 cm nanoparticle compared to the closer one.

The significantly low value for the Gibbs free energy for the nanoparticle is expected since its growth is a three step process. The first step is nucleation, followed by diffusion, and finally controlled by agglomeration. Since the growth of the nanoparticles takes place over a very short time period (e.g., a few milliseconds), the chances of agglomeration are assumed to be minimal. Diffusion, however, still plays a critical role in determining the size of the nanoparticles. The rate of increase in the radius of the nanoparticle, due to diffusion, is guided by the following equation:

$$\frac{dr}{dt} = D(C - Cs)\frac{V_m}{r} \quad (3)$$

The variable D is the Diffusion constant, C is the bulk concentration, $C_s$ is the surface concentration, and $V_m$ is the molar volume of the nanoparticle. Equation (3) may be used to determine the ammunition type, since the Diffusion constant D depends on the ammunition. Assuming a standardized Diffusion constant of $200 \times 10^{12}$ m²/s and a concentration distribution proportional to the volume and surface of the sphere, the rate of increase of the nanoparticle is calculated to be 500 nm/sec. Using this simplified theory, the nanoparticle closest to the gun would have increased by 1.35 nm while the furthest nanoparticle would have increased by 4.25 nm. It is too simplistic to assume that the growth rate is identical for both particles; however, it explains the increase in the particle size with distance. Also the Colt has 10 times more energy than the Winchester, which means that in the VLS mechanism, the supersaturated Colt spherical nanoparticle has 30% greater surface energy than the Winchester. This difference leads to a larger diameter nanoparticle for the Colt initially. The slower growth of the Colt nanoparticles implies that the diffusion rate for them is less than that of Winchester. This difference can be studied in detail and be used to identify the weapon caliber on analysis of the GSR nanoparticles. The analyses described above may be used for more accurate forensic studies of GSR and may be used to synthesize large quantities of nanoparticles.

According to the system and method disclosed herein, the present invention provides numerous benefits. For example, embodiments of the present invention provide efficient, accurate, and valuable information for forensic studies. Furthermore, embodiments of the present invention provide such information for short ranges.

A method and system for characterizing gun-shot residue has been disclosed. The method includes determining a size and an elemental composition of at least one nanoparticle from the gun shot residue and then computing a temperature of formation of the at least one nanoparticle based on the size and the elemental composition of the at least one nanoparticle. The method further includes utilizing the size, elemental composition, and temperature of formation of the nanoparticle to determine information such as gun information (e.g., gun make, model, and caliber); velocity and temperature of the bullet, distance traveled by the bullet; and the position and the time (e.g., where and when) the bullet was fired. As a result, the method and system provide valuable information for forensic studies.

The present invention has been described in accordance with the embodiments shown. One of ordinary skill in the art will readily recognize that there could be variations to the embodiments, and that any variations would be within the spirit and scope of the present invention. For example, the present invention can be implemented using hardware, software, a computer readable medium containing program instructions, or a combination thereof. Software written according to the present invention is to be either stored in some form of computer-readable medium such as memory or CD-ROM, or is to be transmitted over a network, and is to be executed by a processor. Consequently, a computer-readable medium is intended to include a computer readable signal, which may be, for example, transmitted over a network. Accordingly, many modifications may be made by one of ordinary skill in the art without departing from the spirit and scope of the appended claims.

What is claimed is:

1. A method for analyzing gun-shot residue, the method comprising:
    determining a size of at least one nanoparticle from the gun shot residue using a measurement system, wherein the size corresponds to a weapon caliber; and
    computing a temperature of formation of the at least one nanoparticle based on the size of the at least one nanoparticle using an analysis application, wherein the temperature of formation corresponds to a firing distance, wherein the weapon caliber and firing distance are useful in forensic studies.

2. The method of claim 1 further comprising computing at least one of a velocity and temperature of a bullet based on one or more of the temperature of formation of the at least one nanoparticle, the size of the at least one nanoparticle, and elemental composition of the at least one nanoparticle.

3. The method of claim 2 further comprising computing a distance between a gun that fired the bullet and a point of impact of the bullet where the GSR was collected.

4. The method of claim 3 wherein the distance is 12 feet or less.

5. The method of claim 2 further comprising determining gun information associated with a gun that fired the bullet based on the velocity and temperature of the bullet.

6. The method of claim 5 wherein the gun information comprises one or more of a make, a model, and a caliber.

7. The method of claim 1 wherein the determining comprises utilizing one of a scanning electron microscope (SEM), and an energy dispersive X-ray (EDX) to characterize the least one nanoparticle.

8. The method of claim 7 wherein the utilizing is automated.

9. The method of claim 1 wherein the computing comprises executing an algorithm that computes one or more of a surface energy, a Gibbs free energy change, and a diffusion rate associated with the size, elemental composition, and the temperature of formation of the at least one nanoparticle.

10. A tangible computer-readable storage medium containing program instructions for analyzing gun-shot residue, the program instructions which when executed by a computer system cause the computer system to execute a method comprising:

determining a size of at least one nanoparticle from the gun shot residue using a measurement system, wherein the size corresponds to a weapon caliber; and computing a temperature of formation of the at least one nanoparticle based on the size of the at least one nanoparticle using an analysis application, wherein the temperature of formation corresponds to a firing distance, wherein the weapon caliber and firing distance are useful in forensic studies.

11. The computer-readable medium of claim 10 further comprising program instructions for computing at least one of a velocity and temperature of a bullet based on one or more of the temperature of formation of the at least one nanoparticle, the size of the at least one nanoparticle, and elemental composition of the at least one nanoparticle.

12. The computer-readable medium of claim 11 further comprising program instructions for computing a distance between a gun that fired the bullet and a point of impact of the bullet where the GSR was collected.

13. The computer-readable medium of claim 12 wherein the distance is 12 feet or less.

14. The computer-readable medium of claim 11 further comprising program instructions for determining gun information associated with a gun that fired the bullet based on the velocity and temperature of the bullet.

15. The computer-readable medium of claim 14 wherein the gun information comprises one or more of a make, a model, and a caliber.

16. The computer-readable medium of claim 10 wherein the determining comprises program instructions for utilizing one of a scanning electron microscope (SEM) and an energy dispersive X-ray (EDX) to characterize the least one nanoparticle.

17. The computer-readable medium of claim 16 wherein the utilizing is automated.

18. The computer-readable medium of claim 10 wherein the computing comprises program instructions for executing an algorithm that computes one or more of a surface energy, a Gibbs free energy change, and a diffusion rate associated with the size, elemental composition, and the temperature of formation of the at least one nanoparticle.

19. A computer-implemented system for analyzing gun-shot residue, the system comprising:

a processor;

an measurement system coupled to the processor, wherein the measurement system utilizes the processor to determine a size of at least one nanoparticle from the gun shot residue, wherein the size corresponds to a weapon caliber, wherein an analysis application utilizes the processor to compute a temperature of formation of the at least one nanoparticle based on the size of the at least one nanoparticle, and wherein the temperature of formation corresponds to a firing distance, wherein the weapon caliber and firing distance are useful in forensic studies.

20. The system of claim 19 further comprising the measurement system is utilized for characterizing the at least one nanoparticle.

21. The system of claim 20 wherein the measurement system is automated.

22. The system of claim 20 wherein the measurement system is a scanning electron microscope (SEM).

23. The system of claim 20 wherein the measurement system is an energy dispersive X-ray (EDX).

24. The system of claim 19 wherein the analysis application utilizes the processor to compute at least one of a velocity and temperature of a bullet based on one or more of the temperature of formation of the at least one nanoparticle, the size of the at least one nanoparticle, and elemental composition of the at least one nanoparticle.

25. The system of claim 24 wherein the analysis application utilizes the processor to compute a distance between a gun that fired the bullet and a point of impact of the bullet where the GSR was collected.

26. The system of claim 25 wherein the distance is 12 feet or less.

27. The system of claim 24 wherein the analysis application utilizes the processor to determine gun information associated with a gun that fired the bullet based on the velocity and temperature of the bullet.

28. The system of claim 27 wherein the gun information comprises one or more of a make, a model, and a caliber.

29. The system of claim 19 wherein the analysis application utilizes the processor to execute an algorithm that computes one or more of a surface energy, a Gibbs free energy change, and a diffusion rate associated with the size, elemental composition, and the temperature of formation of the at least one nanoparticle.

* * * * *